United States Patent [19]

Heiss

[11] 4,099,920

[45] Jul. 11, 1978

[54] TEMPERATURE CONTROL AND STIRRING APPARATUS FOR LUMINESCENCE MEASURING PHOTOMETER

[75] Inventor: Louis Robert Heiss, Annapolis, Md.

[73] Assignee: Baxter Travenol Laboratories, Inc., Deerfield, Ill.

[21] Appl. No.: 778,663

[22] Filed: Mar. 17, 1977

[51] Int. Cl.² ............................................. G01N 21/24
[52] U.S. Cl. ................................. 23/253 R; 356/244
[58] Field of Search ............... 23/253 R; 356/85, 244, 356/246

[56] References Cited

U.S. PATENT DOCUMENTS

| | | | |
|---|---|---|---|
| 2,878,106 | 3/1959 | Malmstadt | 23/253 R |
| 3,764,214 | 10/1973 | Heiss | 356/246 X |
| 3,790,346 | 2/1974 | Ritchie | 23/253 R |
| 3,917,404 | 11/1975 | Heiss | 356/85 |

Primary Examiner—Robert M. Reese
Attorney, Agent, or Firm—Henry W. Collins; Thomas R. Vigil; Eugene M. Cummings

[57] ABSTRACT

The apparatus is incorporated in a photometer utilized for measuring luminescence from a liquid sample containing adenosine triphosphate (ATP) and includes a cavity in a rotatable sample tube carrier inside a reaction chamber of the photometer and ports in the wall of the carrier communicating with the cavity, the ports being connected via tubing to a constant temperature liquid circulation system. The apparatus also includes a mechanism for rotating a sample tube received in the sample tube carrier when the sample tube carrier is rotated from a position outside the chamber to a position within the reaction chamber where a reagent can be inserted into the tube. The rotating mechanism provides for thorough stirring and mixing of the liquid contents of the sample tube and includes a rotatable journaled socket member at the bottom of the opening in the carrier for receiving the sample tube. This socket member has a friction surface in a socket cavity thereof for engaging and holding the sample tube in place and a friction surface on the exterior thereof which engages a rotatably driven shaft when the tube is moved to the position within the reaction chamber for receiving a reagent.

10 Claims, 8 Drawing Figures

TEMPERATURE CONTROL AND STIRRING APPARATUS FOR LUMINESCENCE MEASURING PHOTOMETER

BACKGROUND OF THE INVENTION

1. Field of the Invention

The present invention relates to an improvement to and/or an accessory for a photometer adapted to detect luminescence from a liquid sample when luciferin or luciferase is added to a liquid solution containing adenosine triphosphate (ATP), an energy-storage compound that is present in all living cells. More specifically, the present invention relates to apparatus for maintaining constant the temperature of the liquid sample in a sample tube and for stirring and mixing the liquid sample in the sample tube when the tube is moved to a position within a reaction chamber of the photometer and beneath an opening through which a reagent is inserted into the sample tube.

2. Description of the Prior Art

Heretofore, photometer devices have been proposed having structure for moving a sample tube with a liquid sample therein from a position outside of a reaction chamber to an enclosed and darkened position within the chamber where a photomultiplier tube is positioned and where the tube is beneath a shielded opening at the top of the chamber through which a reagent such as luciferase can be inserted into the tube. An example of such a device is disclosed in U.S. Pat. No. 3,764,214.

In the previous devices it has been common to use some form of temperature control system for controlling the temperature of the liquid sample in the sample tube. See, for example, U.S. Pat. No. 3,917,404. As will be explained in greater detail hereinafter, the present invention provides a temperature control system which can be utilized in a standard rotatable sample tube carrier and which is believed to be simpler and less expensive than previous temperature control systems for photometers.

Also, it has heretofore been proposed to use a magnetic stirring device for stirring the liquid contents of the sample tube. Such a magnetic stirring device creates electrical interference which adversely affects the electronic circuitry of the photometer. As will be explained in greater detail hereinafter, the present invention provides a mechanical apparatus for stirring the sample tube after it is moved from a position outside the reaction chamber to a position within the reaction chamber and beneath the opening through which reagent is inserted into the sample tube.

SUMMARY OF THE INVENTION

According to the invention there is provided in a photometer device which is particularly adapted for sensing the luminescence emitted when a reagent is inserted in a solution containing adenosine triphosphate (ATP) and which includes a reaction chamber mounted on top of a cabinet which has electronic circuitry therein and an indicating meter and control knobs on one side thereof, a photomultiplier tube extending upwardly into the center of the reaction chamber, an opening in the top of the reaction chamber, a rotatable sample tube carrier having a portion thereof positioned outside of the reaction chamber, the portion outside the reaction chamber having a sample tube receiving opening therein, an arm extending from the carrier for rotating the carrier with the sample tube therein into the reaction chamber to a position beneath the opening in the top thereof for receiving a reagent, and said carrier having a light transmitting passageway in the body thereof between the sample tube and the photomultiplier tube, the improvement comprising means coupled to and rotatable with the carrier for maintaining the liquid contents of the sample tube at a desired temperature.

Also, according to the invention, there is provided in the photometer device another improvement comprising means situated exterior of the sample tube for mechanically mixing and stirring the liquid contents of the sample tube after the tube is moved to a desired position within the reaction chamber.

DESCRIPTION OF THE PREFERRED EMBODIMENTS

Figure 1:
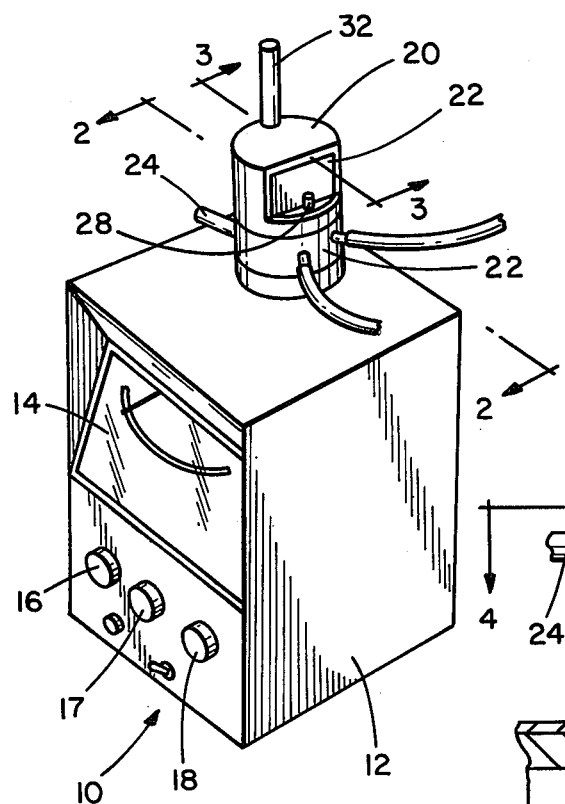
FIG. 1 is a perspective view of a photometer incorporating the apparatus of the present invention.

Referring now to the drawings in greater detail, there is illustrated in FIG. 1 a photometer generally identified by the reference No. 10 and incorporating therein the apparatus of the present invention. The photometer 10 is of the type which is sold under the trademark AMINCO CHEM-GLO and which is manufactured by the American Instrument Company, a division of Baxter Travenol Laboratories, Inc. Such a photometer includes a cabinet 12 having a front side with an indicating meter 14 and control knobs 16, 17 and 18. On top of the cabinet 12 is a generally cylindrical reaction chamber 20 which has a corner thereof cut off so as to facilitate mounting of a rotatable drum or sample tube carrier 22 therein. The sample tube carrier 22 is rotatable 180° within the reaction chamber 20 and has an arm 24 for facilitating rotation thereof.

The carrier 22 has an opening 26 (FIG. 3) therein for receiving a sample tube 28. When the carrier 22 is rotated 180°, the sample tube 28 is moved into the reaction chamber to a position beneath an opening 30 (FIG. 3) in the top thereof through which a reagent can be inserted into the tube 28. In the illustrated embodiment, a light shielding and syringe holding tube 32 is mounted in the opening 31.

Figure 3:
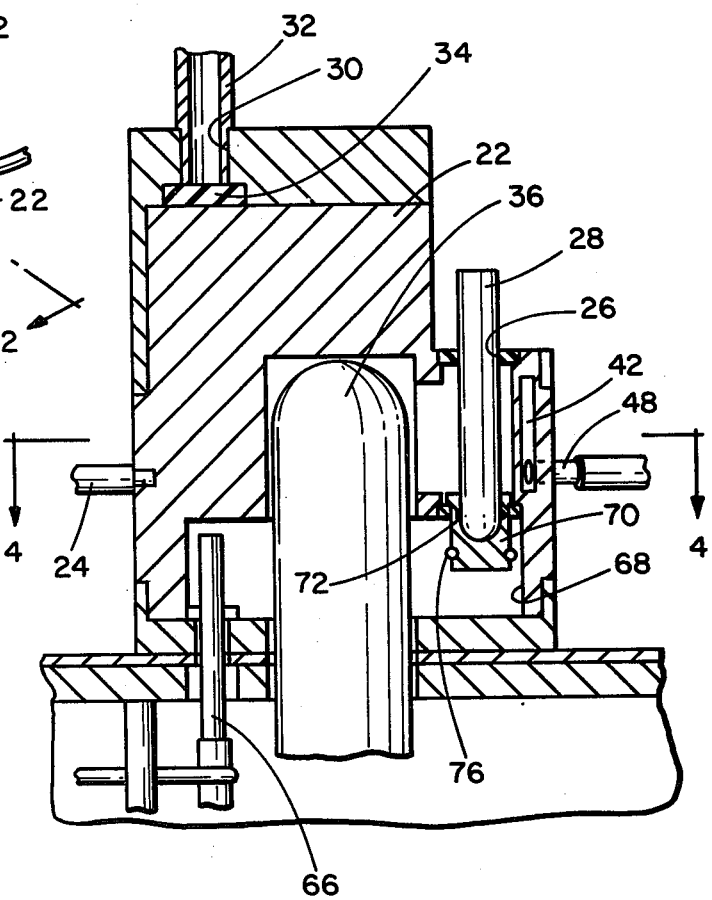
FIG. 3 is a fragmentary sectional view of the reaction chamber and showing a rotatable sample tube carrier therein in one position and is taken along line 3—3 of FIG. 1.

Also, as best shown in FIG. 3 the opening 30 has an elastic plug therein through which a syringe can be inserted to insert reagent into the sample tube 28. The plug 34 and the light shielding tube 32 ensure that the reaction chamber 20 is completely darkened.

As best shown in FIG. 3, a photomultiplier tube 36 is mounted within the cabinet 12 and extends upwardly in the center of the reaction chamber 20.

Figure 5:
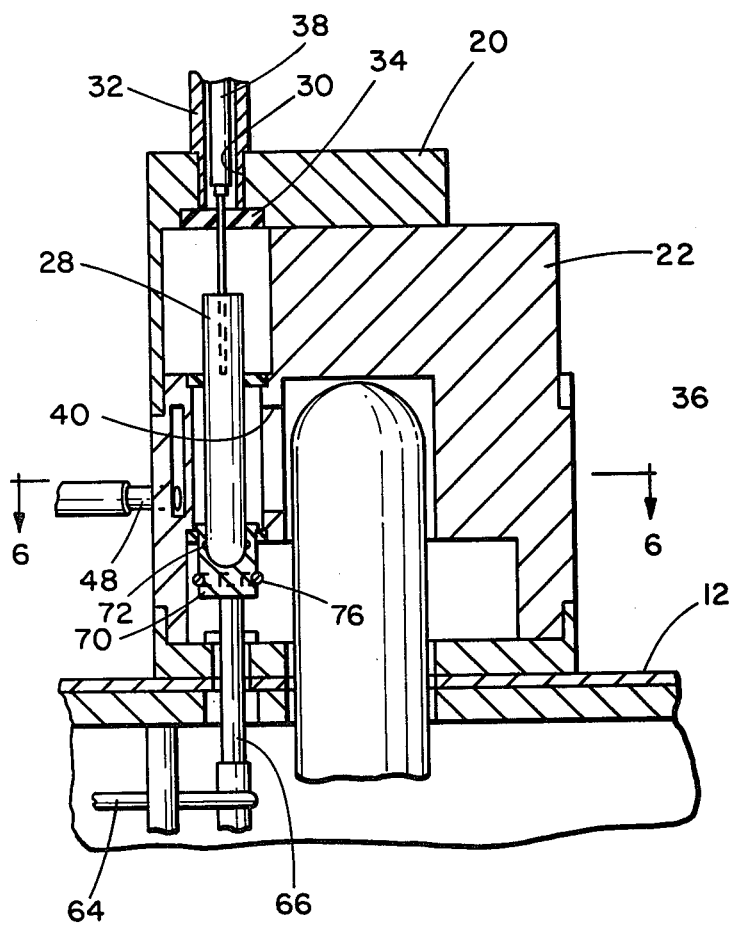
FIG. 5 is a sectional view similar to the view shown in FIG. 3 but showing the sample tube carrier rotated 180° to another position thereof.

When the arm 24 is manipulated to rotate the carrier 22 180°, the sample tube 28 is brought within the reaction chamber 20 and beneath the reagent receiving opening 30 as shown in FIG. 5. At this point, a syringe 38 can be received in the tube 32 and through the plug 34 to insert a reagent into the tube 28 which contains a liquid sample which may have ATP therein. If there is ATP within the liquid the reaction thereof with the reagent, such as luciferase, will create a luminescence which passes through a light transmitting passageway 40 within the body of the carrier 22 to the photomultiplier tube 28. It will be understood that the amount of luminescence given off by the liquid sample in the sample tube 28 and as measured by the photomultiplier 36 will be shown on the indicating meter 14. The indication on the meter 14 can then be utilized to determine the amount of living cells in the liquid sample, e.g., the amount of bacteria in the liquid sample.

In accordance with one aspect of the teachings of the present invention, the carrier 22 is constructed in a manner to facilitate temperature control of the liquid contents of the sample tube 28. Such temperature control is obtained by forming a closed cavity 42 within the carrier 22 and adjacent the sample tube receiving opening 26. Also the sample tube carrier 22 is provided with an input port and an output port 46 formed in the body thereof and communicating with the cavity 42. A fitting 48 or 50 is received in each one of the ports 44 and 46 and is adapted to receive thereon one of two tubings 52 or 54 from a constant-temperature water circulating system (not shown). In this way the temperature of the body of the carrier 22 in the area adjacent the sample-tube-receiving opening 26 therein is maintained relatively constant thereby to control and to maintain the temperature of the liquid contents of the sample tube 28 at a desired temperature.

With the construction just described, the temperature maintaining arrangement or system is rotated with the sample tube 28 when the carrier 22 is rotated. Also the construction of the temperature maintaining system is very simple consisting of the cavity 42, the ports 44 and 46 and the fittings 48 and 50 by which a constant-temperature water circulating system of known type can be simply and easily connected thereto.

In accordance with another aspect of the teachings of the present invention, a mechanical mixing and stirring apparatus 58 is mounted within the cabinet 12 and reaction chamber 20.

Figure 2:
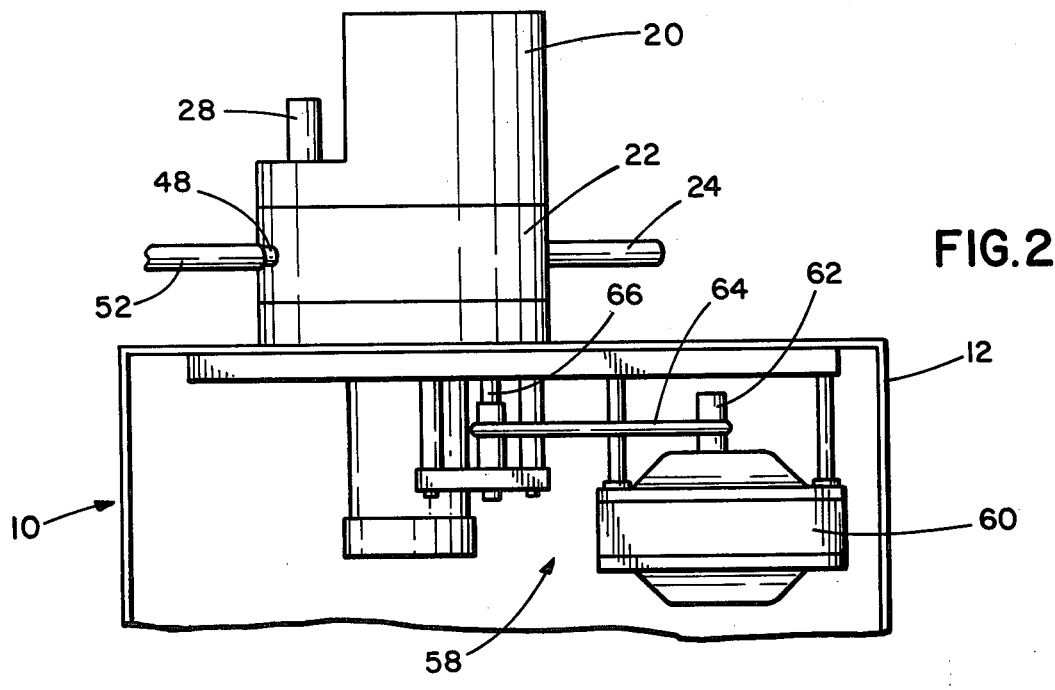
FIG. 2 is a fragmentary vertical plan view of the back side of the photometer shown in FIG. 1 and is taken along line 2—2 of FIG. 1.

The mechanical mixing and stirring mechanism 58 includes an electric motor 60 mounted within the cabinet 12 as best shown in FIG. 2. An output shaft 62 of the motor 60 is connected by a continuous belt 64 to a rotatably journaled shaft 66. The rotatably journaled shaft 66 extends upwardly from the cabinet 12 into the lower end of the reaction chamber 20 and into a cylindrical cavity 68 within the carrier 22. The mechanism 58 also includes a socket member 70 which is rotatably journaled in the carrier 22 at the bottom of the sample tube receiving opening 26 as best shown in FIGS. 3 and 5. The socket member 70 has a resilient "O" ring 72 in a socket cavity 74 thereof for frictionally receiving and holding the bottom of the sample tube 28 in the socket member 70. Also, on the exterior lower side surface of the socket member 70 is received a resilient "O" ring 76 which engages the upper end of the shaft 66.

Figures 4, 6:
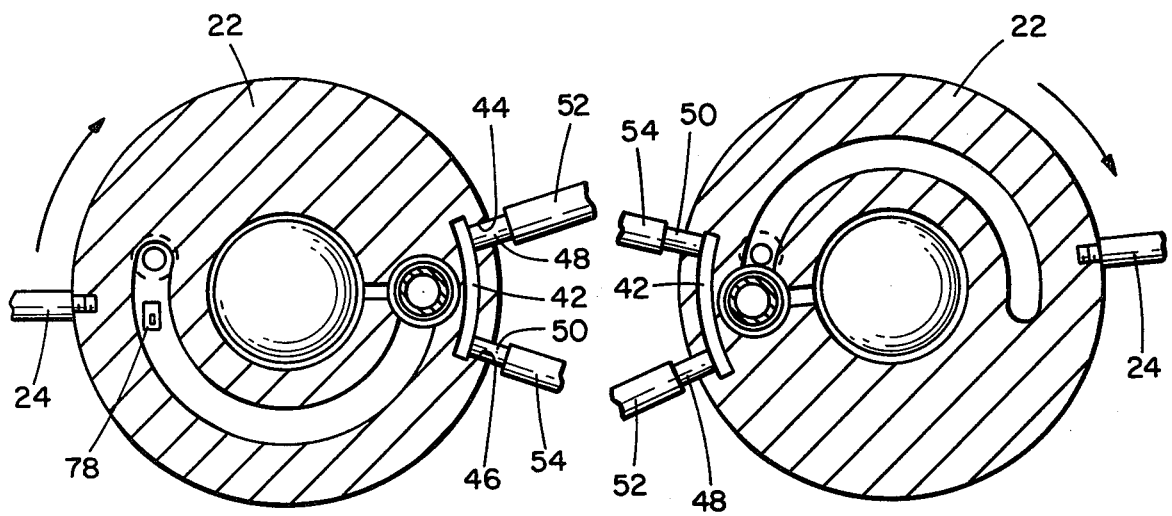
FIG. 4 is a sectional view of the sample tube carrier shown in FIG. 3 and is taken along line 4—4 of FIG. 3.
FIG. 6 is a sectional view of the sample tube carrier taken along line 6—6 of FIG. 5.

When the shaft 66 is rotating and the "O" ring 76 is in engagement therewith the socket member 70 is rotated thereby to rotate the sample tube 28 and mix and stir the liquid contents thereof. This is accomplished only after the carrier 22 is rotated from the position thereof shown in FIGS. 3 and 4 to the position thereof shown in FIGS. 5 and 6 where the sample tube 28 is beneath the reagent insertion opening 30. In travelling to this position, the socket member 70 will engage a limit switch 78 mounted on the bottom of the reaction chamber 20 and extending upwardly into the cavity 78 as best shown in FIG. 4. In this way the mechanism 58 is only operated when the socket member 70 passes thereover as the sample tube 28 is brought into its reaction position underneath the reagent insertion opening 30. Then, of course, when the carrier 22 is rotated from the position shown in FIGS. 5 and 6 back to the position thereof shown in FIGS. 3 and 4 the limit switch 78 is again engaged to turn off the motor 60.

Figure 7:
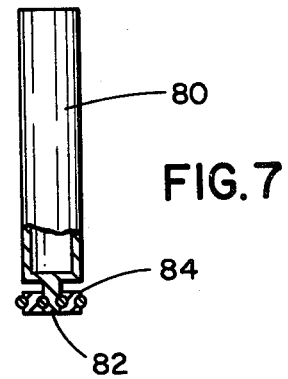
FIG. 7 is a vertical plan view of another type of sample tube and mounting socket used in the photometer with portions broken away.

In FIG. 7 is shown another type of sample tube 80 which is made of polystyrene and which has a boss 82 extending from the lower end thereof. When this type of tube is utilized a different type of socket member 84 is rotatably journaled within the carrier 22.

Figure 8:
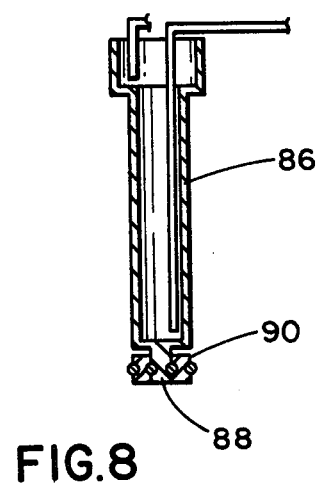
FIG. 8 is a vertical sectional view of still another type of sample tube and mounting socket used in the photometer for flow systems.

FIG. 8 illustrates another type of sample tube 86 which has an enlarged top for receiving sample and reagent tubes therein. This sample tube 86 also has a boss 88 at the bottom thereof which is received into another form of socket member 90.

It will be apparent from the foregoing description that the apparatus of the present invention has a number of advantages, some of which have been described above and others of which are inherent in the invention. Also, obvious modifications and variations can be made to the apparatus of the present invention without departing from the scope of the invention. Accordingly, the scope of the invention is only to be limited as necessitated by the accompanying claims.

I claim:

1. In a photometer device which is particularly adapted for sensing the luminescence emitted when a reagent is inserted in a solution containing adenosine triphosphate (ATP) and which includes a reaction chamber mounted on top of a cabinet which has electronic circuitry therein and an indicating meter and control knobs on one side thereof, a photomultiplier tube extending upwardly into the center of the reaction chamber, an opening in the top of the reaction chamber, a rotatable sample tube carrier having a portion thereof received within the reaction chamber and a portion thereof positioned outside of the reaction chamber, the portion outside the reaction chamber having a sample tube receiving opening therein, an arm extending from the carrier for rotating the carrier with a sample tube therein into said reaction chamber to a position beneath the opening in the top thereof for receiving a reagent, and the carrier having a light transmitting passageway in the body thereof between the sample tube and the photomultiplier tube, the improvement comprising means coupled to and rotatable with the carrier for maintaining the liquid contents of the sample tube at a desired temperature and means situated exterior of the sample tube for mechanically mixing and stirring the liquid contents of the sample tube after the tube is rotated to a desired position within the reaction chamber.

2. In a photometer device which is particularly adapted for sensing the luminescence emitted when a reagent is inserted in a solution containing adenosine triphosphate (ATP) and which includes a reaction chamber mounted on top of a cabinet which has electronic circuitry therein and an indicating meter and control knobs on one side thereof, a photomultiplier tube extending upwardly into the center of the reaction chamber, an opening in the top of the reaction chamber, a rotatable sample tube carrier having a portion thereof received within the reaction chamber and a portion thereof positioned outside of the reaction chamber, the portion outside the reaction chamber having a sample tube receiving opening therein, an arm extending from the carrier for rotating the carrier with a sample tube therein into said reaction chamber to a position beneath the opening in the top thereof for receiving a reagent, and the carrier having a light transmitting passageway in the body thereof between the sample tube and the photomultiplier tube, the improvement comprising means coupled to and rotatable with the carrier for maintaining the liquid contents of the sample tube at a desired temperature.

3. The photometer device according to claim 2 wherein said means for maintaining the liquid contents of the sample tube at a desired temperature includes a closed cavity within the rotatable carrier adjacent the opening for receiving the sample tube, an input port and an outlet port in the carrier communicating with said cavity, and a fitting rotatable with the carrier and extending from each port for connecting each port to one of two flexible tubings leading to a constant temperature liquid circulating system.

4. In a photometer device which is particularly adapted for sensing the fluorescence emitted when a reagent is inserted in a solution containing adenosine triphosphate (ATP) and which includes a reaction chamber mounted on top of a cabinet which has electronic circuitry therein and an indicating meter and control knobs on one side thereof, a photomultiplier tube extending upwardly into the center of the reaction chamber, an opening in the top of the reaction chamber, a rotatable sample tube carrier having a portion thereof received within the reaction chamber and a portion thereof positioned outside of the reaction chamber, the portion outside the reaction chamber having a sample tube receiving opening therein, an arm extending from the carrier for rotating the carrier with a sample tube therein into said reaction chamber to a position beneath the opening in the top thereof for receiving a reagent, and the carrier having a light transmitting passageway in the body thereof between the sample tube and the photomultiplier tube, the improvement comprising means situated exterior of the sample tube for mechanically mixing and stirring the liquid contents of the sample tube after the tube is rotated to a desired position within the reaction chamber.

5. The photometer device according to claim 4 wherein said means situated exterior of the sample tube for mechanically mixing and stirring the liquid contents of the sample tube includes a socket member rotatably journaled within the carrier at the lower end of the sample tube receiving opening, said socket member having means for frictionally engaging the bottom of a sample tube inserted therein, and means for rotating said journaled socket member.

6. The photometer device according to claim 5, wherein said rotating means includes a rotatably journaled shaft extending upwardly from the cabinet into the reaction chamber for engaging said socket member when the carrier is rotated to bring the sample tube into the position within the reaction chamber where a reagent can be inserted therein, an electric motor having an output shaft, and means drivingly coupling said output shaft to said rotatably journaled shaft.

7. The photometer device according to claim 6 wherein said motor is mounted within said cabinet and said coupling means includes a continuous belt between said shafts.

8. The photometer device according to claim 5 wherein said friction means within and socket member includes an "O" ring in the side wall of a socket cavity in said socket member.

9. The photometer device according to claim 8 wherein said mechanical mixing and stirring means includes an "O" ring around the exterior of said socket member to facilitate the driving of same by a rotatable shaft extending upwardly from the cabinet into the reaction chamber and forming part of said means for rotating said socket member.

10. The photometer device according to claim 8 wherein said mechanical mixing and stirring means includes a limit switch mounted within said reaction chamber in position to be engaged and actuated when the sample tube is moved from outside the reaction chamber to a position within the reaction chamber underneath the reagent insertion opening.

* * * * *